United States Patent [19]
de la Torre et al.

[11] Patent Number: 5,630,825
[45] Date of Patent: May 20, 1997

[54] MAGAZINE FOR LOADING A NEEDLE ONTO A STITCHING INSTRUMENT AND FOR LOADING A LENGTH OF SUTURE ONTO A SUTURE DISPENSING INSTRUMENT

[76] Inventors: Roger A. de la Torre, 48 Dauphine Dr., Lake St. Louis, Mo. 63367; James S. Scott, 131 Muirfield Crest Ct., St. Charles, Mo. 63304; James E. Jervis, 495 Walsh Rd., Atherton, Calif. 94027

[21] Appl. No.: 429,822

[22] Filed: Apr. 27, 1995

[51] Int. Cl.⁶ .................................................. A61B 17/00
[52] U.S. Cl. .................. 606/148; 606/139; 206/339; 206/438; 206/63.3
[58] Field of Search ..................... 606/144–148, 606/139, 1; 112/169, 80.03; 206/63.3, 338–341, 346, 380, 382, 383, 438; 221/191

[56] References Cited

U.S. PATENT DOCUMENTS

| | | | |
|---|---|---|---|
| 2,910,066 | 10/1959 | Kammer | 606/147 |
| 5,454,822 | 10/1995 | Schöb et al. | 606/148 |
| 5,458,609 | 10/1995 | Gordon et al. | 606/144 |
| 5,472,081 | 12/1995 | Kilgrow et al. | 206/63.3 |
| 5,472,446 | 12/1995 | De La Torre | 606/144 |
| 5,478,344 | 12/1995 | Stone et al. | 606/144 |
| 5,478,345 | 12/1995 | Stone et al. | 606/144 |

*Primary Examiner*—Jeffrey A. Schmidt
*Attorney, Agent, or Firm*—Howell & Haferkamp, L.C.

[57] ABSTRACT

The present invention pertains to a magazine that is loaded with a needle and an attached length of suture pre-tied in a knot on the magazine. The magazine is used in loading the needle onto a stitching surgical instrument and in loading the tied length of suture onto a suture tying surgical instrument.

15 Claims, 3 Drawing Sheets

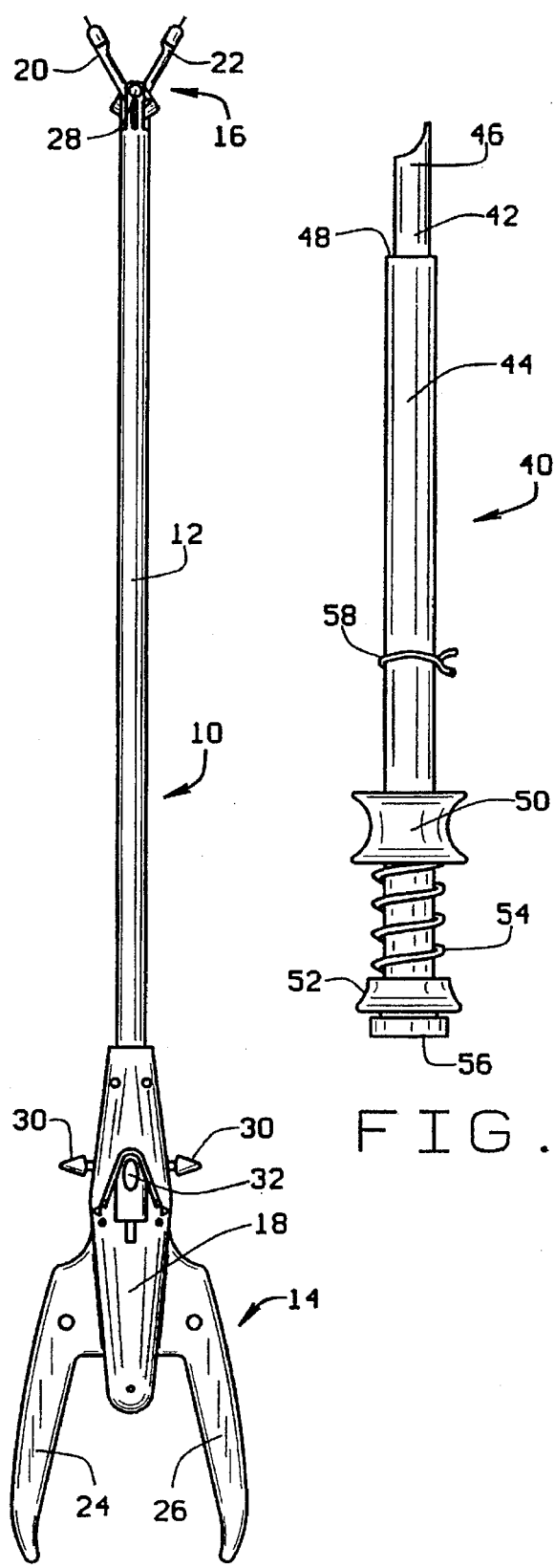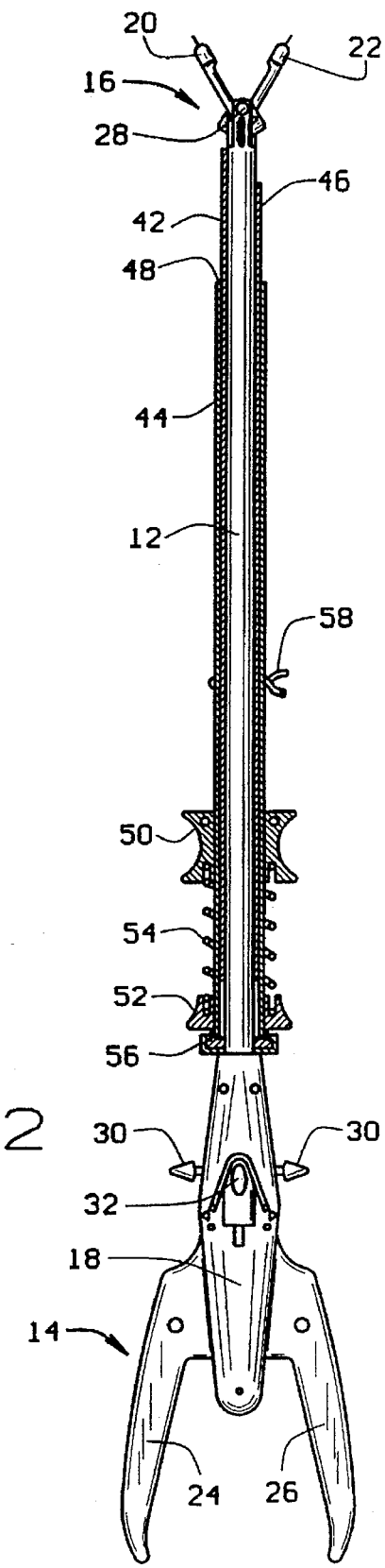
FIG. 1　　FIG. 2　　FIG. 3

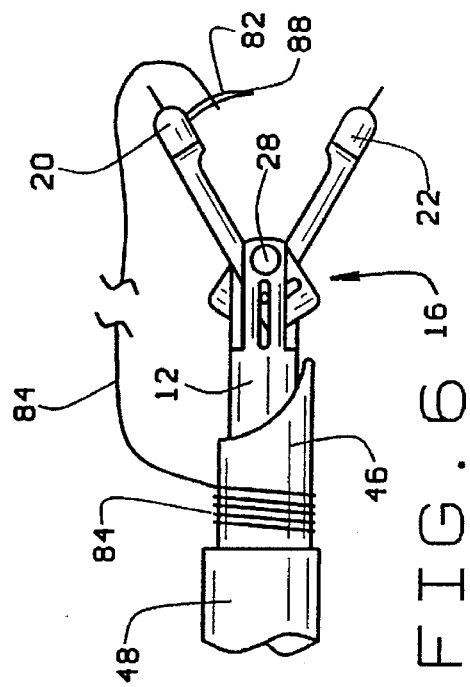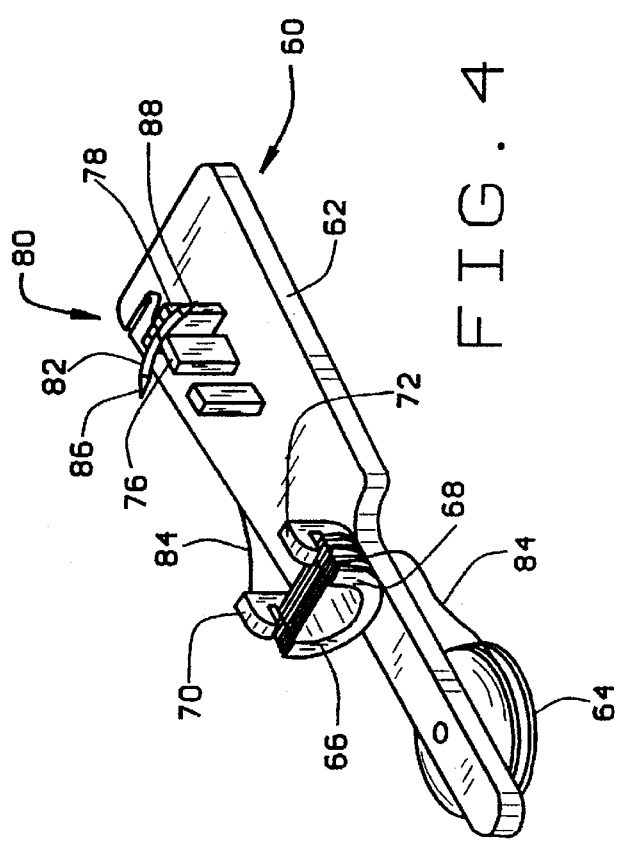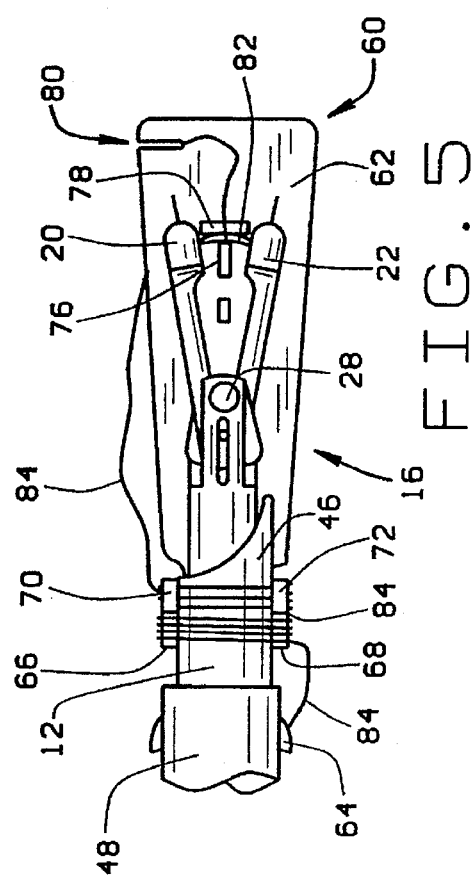

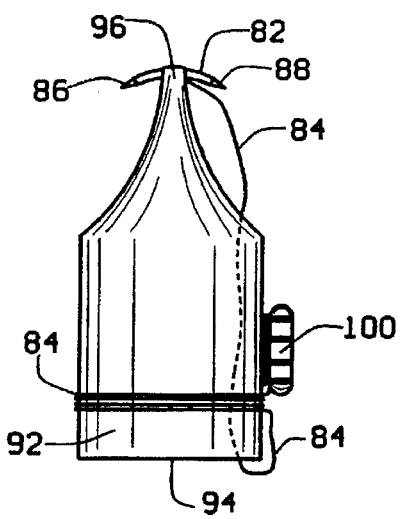 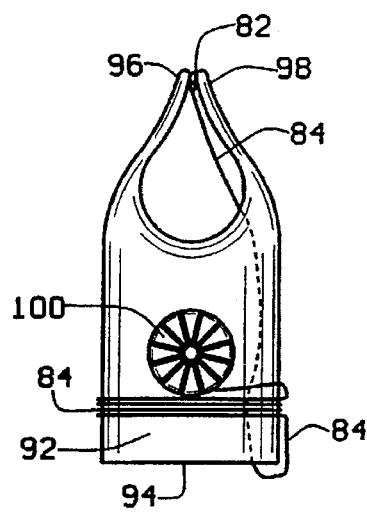
FIG. 7  FIG. 8
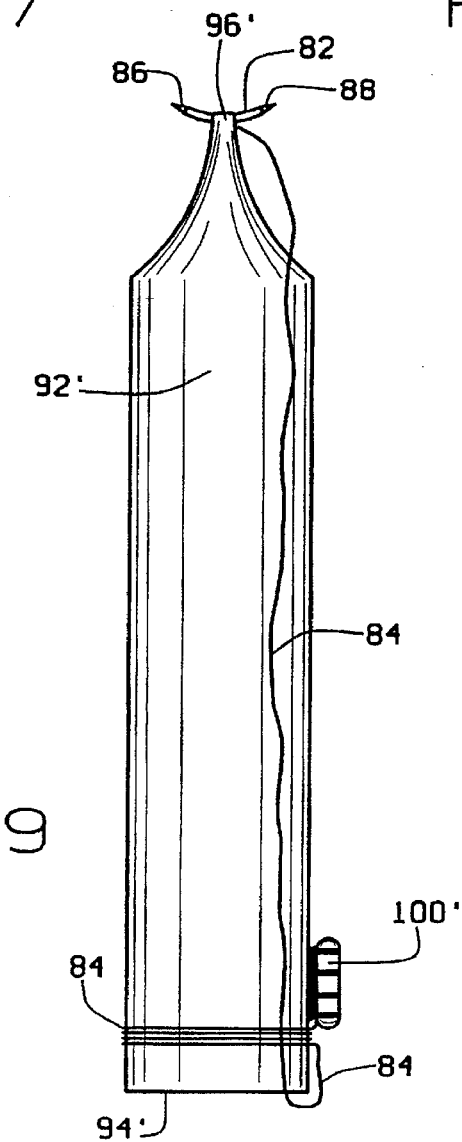
FIG. 9

MAGAZINE FOR LOADING A NEEDLE ONTO A STITCHING INSTRUMENT AND FOR LOADING A LENGTH OF SUTURE ONTO A SUTURE DISPENSING INSTRUMENT

BACKGROUND OF THE INVENTION

1. Field of the Invention

The present invention pertains to a magazine that stores a needle and an attached length of suture pre-tied in a knot on the magazine. The invention also pertains to the method of using the magazine in loading the needle onto a stitching surgical instrument and in loading the tied length of suture onto a suture dispensing surgical instrument.

2. Description of the Related Art

Various different types of surgical instruments specifically designed for use in minimally invasive surgery are known in the prior art. These instruments are designed for use in laparoscopic surgical procedures where small incisions are made and a remote surgical site within the body is accessed through a cannula inserted through the incision.

One such surgical instrument is the Auto Suture® Endo Stitch® of United States Surgical Corporation. This instrument is comprised of an elongate tube having a pair of opposed handle levers at its proximal end and a pair of opposed arms at its distal end. The pair of arms project from the distal end in a V-shaped configuration in the at rest position of the arms. The surgeon squeezes the opposed handle levers at the instrument proximal end to cause the pair of arms to pivot through arcs toward each other at the instrument distal end. Each of the arms have apertures in their opposing surfaces that contain mechanisms for gripping a needle specifically designed for use with the instrument.

The needle has a slight curvature and tips at its opposite ends. A length of suture is attached to the needle intermediate its ends. When grasping the needle with the instrument, the needle is first positioned between the opposing surfaces of the instrument arms. The handle levers of the instrument are then manipulated toward each other to cause the two arms to pivot through their arc segments toward each other. The points at the needle opposite ends are received into the apertures in the instrument arms as the arms move toward each other. The gripping mechanism in one of the arms grasps the tip of the needle inserted into the aperture of that arm. When the handle levers are released causing the pair of arms to pivot back to their at rest positions where the arms form the V-shaped configuration, the needle remains grasped in the aperture of the one arm. Subsequent manipulation of the instrument handles toward each other will cause the needle to be passed back and forth between the apertures of the two arms with the grasping mechanisms of the two arms alternatively grasping the opposite tips of the needle.

The above-described instrument is specifically designed to be inserted through a cannula and used in placing stitches at a remote location within the body. In use, the body tissue to be stitched is positioned between the arms with the arms in their at rest V-shaped configuration. The handle levers are manipulated toward each other by the surgeon causing the exposed needle tip to pass through the tissue and into the aperture of the instrument arm not holding the needle. That arm then grasps the needle tip inserted into its aperture. The handle levers are then manipulated by the surgeon to cause the arms to return to their at rest, V-shaped positions. This causes the arm now grasping the needle to pull the needle and the attached length of suture through the tissue thereby forming a first stitch in the tissue. The procedure is repeated passing the needle through the tissue and alternatively grasping the needle with the two arms of the instrument. When the number of desired stitches have been placed, the suture ends may be tied off by any of several means. For example, the needle can be cut from the suture and removed and the suture tied in a knot at the surgical location, usually using conventional graspers.

Many prior art instruments have been developed to facilitate tying knots in suture material at surgical sites located in remote areas that are difficult to access. Several of these instruments are specifically designed for use in laparoscopic surgical procedures where the instrument is inserted through a cannula to the surgical site. An example of such an instrument is that disclosed in U.S. Pat. No. 5,391,176, incorporated herein by reference. Other examples of surgical instruments of this type that are specifically designed for tying a knot in a length of suture at a remote location are disclosed in pending U.S. patent applications Ser. No. 08/277,987, filed Jul. 20, 1994, now U.S. Pat. No. 5,527,323 and Ser. No. 08/377,362, filed Jan. 24, 1995, both of which are assigned to the assignee of this application and both of which are incorporated herein by reference. Generally, the knot-tying instruments of this type are comprised of an elongate tube having opposite proximal and distal ends and an interior bore extending through the tube and dimensioned sufficiently large for insertion of another surgical instrument therethrough. The suture-tying instrument is loaded with a length of suture wrapped around its distal end. The length of suture is pre-tied on the distal end of the instrument in one or more knots. A free end of the length of suture extends from the pre-tied knots and is secured to the length of the knot-tying instrument. The opposite end of the length of suture is attached to a needle.

In use of the suture-dispensing instrument, the distal end of the instrument is first inserted through the cannula to position the distal end at the surgical location where it is desired to place one or more stitches in body tissue. The needle is grasped by a separate surgical grasper and passed through the tissue the desired number of times to place the desired stitches. The needle, with the length of suture still attached, is then removed from the surgical site through the interior bore of the knot-tying instrument. The loops of suture wrapped in a knot on the distal end of the instrument are then displaced off the instrument over the length of suture extending from the stitches. The suture extending from the knots is then pulled tight, thereby forming a knot in the suture at the location of the stitches.

Using the Auto Suture® Endo Stitch® in combination with the above-described knot-tying surgical instrument enables the surgeon to easily place a desired number of stitches at a remote surgical location and then tie a knot in the suture. In combination, the interior bore of the knot-tying instrument must be dimensioned sufficiently large to insert the Auto Suture® Endo Stitch® stitching instrument through the interior bore of the knot-tying instrument so that its arms project from the distal end of the knot-tying instrument. The needle with the attached length of suture specifically designed for use with the stitching instrument is then attached to one of the arms of the instrument in the manner described above. However, in order to use these two instruments together taking full advantage of the benefits offered by the two instruments, the length of suture extending from the needle must then be wrapped in a knot on the distal end of the suture-dispensing instrument and the free end of the suture then extended from the knot and secured to the knot-tying instrument.

A magazine apparatus that could be used to quickly load a needle onto the stitching instrument and then load a length of pre-tied suture onto the end of the knot-tying instrument would significantly enhance the benefits provided to the surgeon by these two instruments.

SUMMARY OF THE INVENTION

The magazine apparatus of the invention is designed to store thereon a needle of the type used with the Auto Suture® Endo Stitch® stitching surgical instrument of United States Surgical Corporation, together with a length of suture attached to the needle. The apparatus stores the length of suture in one or more pre-tied knots on the apparatus. Using the apparatus in practicing the method of the invention, the needle and attached length of suture are loaded onto the stitching instrument and a knot-tying instrument through which the stitching instrument has been inserted. The needle is loaded onto one of the two arms of the stitching instrument and the length of suture tied in one or more knots is loaded onto the distal end of the knot-tying instrument.

In various embodiments of the magazine apparatus of the invention, the needle is supported on the magazine with its opposite tips exposed so that it can be easily grasped at one of its tips by one of the arms of the stitching instrument. In one embodiment of the magazine, it is provided with a pair of opposed sidewalls around which the suture is wrapped in at least one knot. In further embodiments of the magazine, the magazine is formed with a tubular portion around which the length of suture is wrapped in at least one knot. Each of the embodiments also includes a spool or bobbin around which is wrapped an additional length of suture leading to the free end of the suture.

In use, the stitching instrument is first inserted through the center bore of the knot-tying instrument so that the arms of the stitching instrument project from the distal end of the knot-tying instrument. The stitching instrument handle levers are operated by the surgeon to pivot the pair of arms of the instrument to their mutually opposed, adjacent positions. The arms of the instrument are then inserted through the magazine opposed sidewalls or magazine tubular portion, and thereby the arms are inserted through the knot wrapped in the suture around the magazine. The arms of the stitching instrument are then caused to move to their V-shaped, at rest positions by manipulating the handle levers of the instrument. The arms are next moved adjacent the needle held on the magazine so that the needle is positioned between the apertures of the two arms. Again, the handle levers of the instrument are manipulated to cause the two arms to move toward each other, thereby gripping one of the tips of the needle in the apertures of the two arms.

Next, the knot tied in the suture around the magazine is slipped off an end of the magazine and onto the distal end of the knot-tying instrument. The needle is then pulled from the magazine while held between the two arms of the stitching instrument, thereby completing the loading of the knot tied in the suture on the knot-tying instrument and the loading of the needle connected to the suture on the stitching instrument. The free end of the suture is then anchored near the proximal end of the knot-tying instrument.

In the embodiment of the magazine having opposed sidewalls, the above-described loading of the suture on the knot-tying instrument and the needle on the stitching instrument completely disconnects the magazine from these two instruments. In embodiments of the magazine having a tubular portion around which the knot in the suture is wrapped, after the suture knot is loaded on the knot-tying instrument and the needle loaded on the stitching instrument, the tubular portion of the magazine is slipped over the ends of these two instruments to disconnect the magazine from the instruments and complete the loading of the suture and needle.

In a still further embodiment of the magazine of the invention, the stitching instrument and knot-tying instrument are inserted into a tubular portion of the magazine and the knot tied in the suture around the tubular portion is slipped off the magazine onto the knot-tying instrument. The two instruments are then removed from the tubular portion of the magazine and the magazine is turned 180 degrees to present the needle to the stitching instrument. The arms of the stitching instrument are then manipulated as described above to grip the needle between the two arms. The needle is then pulled from the magazine, thereby disengaging the magazine from the instruments and completing the loading of the suture and needle on the instruments.

BRIEF DESCRIPTION OF THE DRAWINGS

Further objects and features of the invention are revealed in the following detailed description of the preferred embodiments of the invention and in the drawing figures wherein:

FIG. 1 shows the Auto Suture® Endo Stitch® stitching surgical instrument;

FIG. 2 shows the knot-tying surgical instrument;

FIG. 3 shows the stitching instrument of FIG. 1 inserted through the center bore of the knot-tying instrument of FIG. 2;

FIG. 4 is a perspective view of a first embodiment of the suture and needle loading magazine of the invention;

FIG. 5 is a partial view of the magazine loading a length of suture and a needle on the stitching instrument and knot-tying instrument of FIGS. 1 and 2;

FIG. 6 is a partial view of the length of suture and needle loaded onto the stitching instrument and knot-tying instrument of FIGS. 1 and 2;

FIGS. 7 and 8 show a further embodiment of the magazine of the invention; and

FIG. 9 shows a still further embodiment of the magazine of the invention.

DESCRIPTION OF THE PREFERRED EMBODIMENTS

The magazine of the invention is specifically designed to store a needle and attached length of suture and to be used, according to the method of the invention, to load the needle onto a stitching instrument and to load the length of suture onto a separate knot-tying instrument. The stitching instrument and knot-tying instrument are not a part of the magazine of the invention or the method of using the magazine. The magazine of the invention is specifically designed for use with a stitching instrument and knot-tying instrument to facilitate the loading of the needle on the stitching instrument and the attached length of suture on the knot-tying instrument. The description of the magazine to follow is with reference to a particular stitching instrument and a particular knot-tying instrument. It should be understood that the description with reference to these two particular instruments is for illustrative purposes only and is not intended to be limiting. The magazine of the invention may be used with other similar types of stitching and knot-tying surgical instruments than those described herein. Various embodiments of the magazine of the invention are shown in FIGS. 4–9. However, to understand why these magazines are designed in the way they are and how these magazines are used, it is first necessary to understand the construction and function of the stitching instrument and knot-tying instrument with which the magazine is used.

In FIG. 1 is shown the Auto Suture® Endo Stitch® stitching surgical instrument 10 of United States Surgical Corporation. Because this instrument is known in the prior art, its construction and operation will be described herein only generally.

The stitching instrument 10 has a longitudinally, elongated tubular body 12 with opposite proximal 14 and distal 16 ends. The proximal end 14 of the body has a handle assembly 18 mounted thereon. The distal end of the body has a pair of arms 20, 22 mounted thereon for pivoting movement relative to the body. A pair of hand levers 24, 26 on the handle assembly 18 manipulate the arms 20, 22. The hand levers and arms are shown in their at rest positions in FIG. 1. By manipulating the hand levers 24, 26 toward each other by squeezing the levers, the pair of arms 20, 22 are caused to pivot about the pivot pin 28 through arc segments moving the two arms toward each other so that they are positioned substantially parallel to the longitudinal axis of the instrument body 12. Releasing the squeeze on the hand levers 24, 26 causes the levers to move apart from each other and causes the arms 20, 22 to pivot back through the arc segments to their at rest positions shown in FIG. 1. A spring mechanism contained within the instrument causes the arms to return to their at rest positions.

A pair of lock tabs 30 are provided on the handle assembly 19. The lock tabs 30 are moved downwardly as viewed in FIG. 1 when the hand levers 24, 26 are squeezed toward each other to lock the arms 20, 22 in their mutually opposed, parallel positions. A release button 32 is also provided on the handle assembly 18. The release button 32 is pressed when the arms 20, 22 are in their locked, parallel positions to release the arms.

Although not shown in FIG. 1, the arms 20, 22 have small apertures in their mutually opposed surfaces. The apertures are dimensioned to receive therein a point of a needle specifically designed to be used with the stitching instrument. The needle has a slight curvature and has points at its opposite ends. When the arms are operated by manipulating the hand levers 24, 26 to move the arms toward each other through their arc segments, positioning the needle between the arms will result in the opposite tips of the needle being received in the two apertures of the arms. A mechanism is provided in each arm to alternately grip the opposite tips of the needle in one of the arms when the arms are manipulated between their closed positions and their at rest positions. This enables the stitching instrument 10 to pass the needle between the two arms 20, 22 as the hand levers 24, 26 are operated.

The knot-tying instrument 40 shown in FIG. 2 is one of the embodiments of knot-tying instruments disclosed in U.S. patent application Ser. No. 08/277,987, filed Jul. 20, 1994, now U.S. Pat. No. 5,527,323, and U.S. patent application Ser. No. 08/377,362, filed Jan. 24, 1995, both of which are assigned to the assignee of the present invention and both of which are incorporated herein by reference.

Generally, the knot-tying instrument 40 is comprised of an inner tubular member 42 and an outer tubular member 44. The inner tubular member has a hollow interior bore dimensioned sufficiently large to permit the insertion of the stitching instrument 10 therethrough. The longitudinal length of the inner tubular member 42 is smaller than that of the body 12 of the stitching instrument so that the distal end 16 of the stitching instrument projects from the distal end 44 of the inner tubular member when the instrument is inserted through the tubular member. The longitudinal length of the inner tubular member 42 is slightly smaller than that of the outer tubular member 44 so that only a knot-pushing projection 48 on the distal end of the inner member will extend out of the distal end 48 of the outer member when the inner member is completely retracted into the outer member.

A handle 50 is mounted for reciprocating movement over the exterior of the outer tubular member 44. The handle 50 is connected through longitudinal slots (not shown) in the outer tubular member 44 to the inner tubular member 42 so that the inner tubular member reciprocates within the outer tubular member in response to the handle being reciprocated over the exterior of the outer tubular member. An end cap 52 is secured to the proximal end of the outer tubular member 44 and a spring 54 is positioned between the end cap 52 and the handle 50. The spring 54 biases the handle 50 and the inner tubular member 42 to their extended positions shown in FIG. 2. A seal 56 having a center aperture is secured over the end cap 52 to effect a seal to the stitching instrument.

In operation of the knot-tying instrument 40, a length of suture is first wrapped over the distal end 46 of the inner tubular member. The length of suture is wrapped in a pattern that will produce a knot in the suture when one end of the suture, having a needle attached thereto, is inserted through the center bore of the inner tubular member 42 from its distal end 46 and the knot wrapped in the suture on the inner member distal end 46 is pushed off the member and onto the length of suture extending into the member interior bore. To push the knot formed on the inner member distal end 46 off the end, the handle 50 is manipulated toward the end cap 52 against the bias of the spring 54. This causes the inner member distal end 46 to be retracted into the outer member 44 so that only the knot-pushing projection extends from the outer member distal end 48. The movement of the outer member distal end 48 over the inner member distal end 46 pushes the knot off of the inner member and onto the length of suture drawn into the interior bore of the inner member.

FIG. 3 shows the relative positions of the stitching instrument 10 and knot-tying instrument 40 when the stitching instrument has been inserted through the interior bore of the knot-tying instrument. In these relative positions of the two instruments, the magazine of the invention may be used according to the method of the invention to load a needle onto one of the arms 20, 22 of the stitching instrument while loading a length of suture attached to the needle and tied in one or more knots onto the inner member distal end 46 of the knot-tying instrument 40.

FIG. 4 shows a first embodiment of the magazine 60 of the invention. In the preferred embodiment, the magazine is constructed entirely of plastic. However, other materials may also be employed. The magazine is comprised of a base 62 having a longitudinal length and a lateral width. At one end of the longitudinal length of the base is a spool 64 secured to the bottom surface of the base for rotation relative to the base. The spool 64 is employed in storing a length of suture as will be explained. Projecting from the top surface of the base intermediate its longitudinal length is a means for holding a length of suture comprised of a pair of sidewalls or projections 66, 68. As best seen in FIG. 4, the projections 66, 68 come together forming a U-shaped channel which is spaced slightly above the top surface of the base. The U-shaped channel positions the projections 66, 68 sufficiently far apart to enable insertion of the distal end of the stitching instrument 10 therethrough. Each of the projections, 66, 68 has a block 70, 72 respectively, formed at its top end. The blocks 70, 72 prevent suture wrapped around the projections from being pushed off of the projections as the stitching instrument 10 is inserted between the projections and through the suture wrapped around the U-shaped channel formed by the projections.

Spaced longitudinally from the projections 66, 68 on the top surface of the base 62 is a means for holding a needle on the base in the form of a pair of needle projections 76, 78. As seen in FIGS. 4 and 5, the needle projections 76, 78 are arranged in a T-shaped configuration with a slight spacing between the two projections. The spacing is dimensioned sufficiently small to wedge the needle between the projections 76, 78. The lateral width dimensions of the needle projections 76, 78 are sufficiently small so that the tips at the needle opposite ends project laterally beyond the two projections.

The base 62 is also provided with a small slot 80 in its side. The slot 80 is provided for insertion of the suture therein to keep the portion of suture extending from the needle to that wrapped around the projections 60, 68 from hanging loose from the magazine.

Shown in FIGS. 4–6 is a needle 82 with attached length of suture 84 of the type employed with the stitching instrument 10. As explained earlier, the needle 82 has tips 86, 88 at its opposite ends and is formed with a slight curvature. The suture 84 is secured to the needle intermediate its opposite tips. The needle 82 is secured to the magazine 60 by being wedged in the space between the needle projections 76, 78. As seen in FIGS. 4 and 5, the needle is secured between these projections at the intermediate portion of the needle so that its opposite tips 86, 88 project laterally from the projections and are readily accessible.

The suture 84 extends from the needle through the slot 80 and then beneath the base 62 to the pair of projections 66, 68 above the top surface of the base. The suture is then wrapped around the U-shaped channel formed by the projections 66, 68 in a pattern of loops that will form a knot in the suture when the needle 82 is inserted through the pattern of loops. There are a variety of different patterns of loops of suture material that may be formed around the projections 66, 68 to produce a knot in the suture when the needle is inserted through the pattern of loops. Several examples of such loop patterns are disclosed in U.S. patent application Ser. No. 08/277,987, now U.S. Pat. No. 5,527,323, and Ser. No. 08/377,362, referred to earlier. From the pattern of loops wrapped around the projections 66, 68, the suture then extends to the spool 64 where the remaining length of suture extending to its free end is wrapped around the spool.

The use of this first embodiment of the magazine 60 according to the method of the invention is illustrated in FIGS. 5 and 6. With the stitching instrument 10 inserted through the center bore of the knot-tying instrument 40, the hand levers 24, 26 of the stitching instrument are manipulated to cause the arms 20, 22 to move through their arc segments to their mutually opposed, parallel positions. The arms are then either held in this position or locked in position by engaging the lock tabs 30 on the stitching instrument. The arms are then inserted through the U-shaped channel formed by the pair of projections 66, 68 and through the pattern of suture loops wrapped around the projections. Once the arms have cleared the suture loops, the handle levers are released or the release button 32 is pressed to cause the arms to be biased to their at rest positions. The stitching instrument and knot-tying instrument are then together inserted further through the projections 60, 68 and the pattern of loops so that the distal end 46 of the knot-tying instrument inner tubular member is inserted between the projections 66, 68 and the pattern of suture loops wrapped around the projections. With this positioning of the inner tubular member distal end 46 relative to the projections 66, 68, the pair of arms 20, 22 of the stitching instrument are positioned on opposite sides of the needle 82 held by the magazine.

The handle levers 24, 26 of the stitching instrument are then squeezed together to cause the arms to pivot toward each other and receive the opposite tips 86, 88 of the needle in their apertures as shown in FIG. 5. The arms are then locked by engaging the lock tabs 30 or the surgeon continues squeezing the hand levers 24, 26 so that the arms 20, 22 hold the needle 82 between their opposed surfaces as shown in FIG. 5. The base 62 of the magazine is then pivoted downwardly from the arms thereby pulling the needle 82 from the spacing between the needle projections 76, 78. The arms are then unlocked and the hand levers 24, 26 are permitted to move away from each other to their at rest positions causing the arms 20, 22 to pivot away from each other to their at rest positions. This results in the needle being held at one of its tips in one of the arm apertures.

Next, the pattern of loops wrapped around the projections 66, 68 is pushed off the projections in a direction away from the blocks 70, 72 and onto the inner tubular member distal end 46 of a knot-tying instrument. This loads the pattern of loops on the knot-tying instrument.

The magazine 60 is then moved toward the proximal ends of the stitching instrument and knot-tying instrument causing a length of suture to be pulled from the spool 64. As the length of suture is pulled from the spool, it pulls tight the knot formed in the suture around the inner tubular member distal end 46 of the knot-tying instrument. The length of suture is wrapped around the cleat 58, and then the suture is cut, freeing the magazine 60 from the suture and completing the loading of the needle and suture on the two instruments from the magazine.

FIGS. 7 and 8 show a further embodiment of the magazine of the invention. In this embodiment, the base 92 has a tubular configuration at its proximal end 94. The base has a hollow interior bore that extends entirely through its longitudinal length. The interior bore is dimensioned sufficiently large to pass the pair of arms 20, 22 of the stitching instrument therethrough with the arms holding the needle 82 between them. The tubular portion of the base adjacent its proximal end 94 functions as the opposed projections 66, 68 of the previously described embodiment as will be explained. In this embodiment, the opposed projections form opposite sides of the tubular portion. As the base extends longitudinally, its configuration changes from tubular to a pair of opposed needle projections 96, 98. As the needle projections extend longitudinally from the tubular portion of the base, they taper toward the center axis of the tubular portion. At the distal ends of the needle projections 96, 98 there is a spacing between the projections dimensioned sufficiently small to wedge the needle 82 therein.

A spool 100 is mounted to the exterior of the base 92 for rotation of the spool relative to the base.

As in the previously described embodiment, the needle 82 with the attached length of suture 84 is mounted and stored on the base 92 of the magazine embodiment of FIGS. 7 and 8. As shown in the drawing figures, the needle 82 is wedged at an intermediate portion of the needle into the spacing between the distal ends of the needle projections 96, 98. The opposite tips 86, 88 of the needle project laterally beyond the needle projections where they can be easily grasped between the arms 20, 22 of the stitching instrument.

The suture 84 extends from the needle 82 through the interior bore of the base 92. The suture emerges from the bore at the proximal end 94 of the base and is wrapped in a pattern of loops around the exterior of the base adjacent its proximal end. As in the previously described embodiment, the pattern of suture loops will produce a knot in the suture when the needle is passed through the center of the loops once mounted on the knot-tying instrument 40. From the pattern of loops, the free end of the suture extends to and is wrapped around the spool 100.

The use of the embodiment of the magazine shown in FIGS. 7 and 8 is similar to the previously described embodiment. Together, the distal ends of the stitching instrument and knot-tying instrument are inserted through the interior bore of the base from its proximal end 94. The arms 20, 22 of the stitching instrument are held in their mutually opposed, parallel positions as they are inserted through the interior bore of the base. As the arms approach the distal ends of the needle projections 96, 98, the hand levers 24, 26 of the stitching instrument are manipulated to cause the arms to pivot open to their V-shaped, at rest configurations. The arms are then positioned on the opposite sides of the needle 82 with the apertures of the arms adjacent the opposite needle tips 86, 88. The hand levers are then again manipulated causing the arms to pivot toward each other and thereby engaging the needle tips 86, 88 in the apertures of the arms.

Next, the pattern of loops of suture 84 is slipped off of the base proximal end 94 onto the distal end 46 of the knot-tying instrument inner tubular member. The stitching instrument 10 and knot-tying instrument 40 are then removed from the interior bore of the base 92. The base is then moved along the longitudinal length of the knot-tying instrument to the cleat 58 while the length of suture wrapped around the spool 100 unwinds from the spool. The length of suture is then secured to the cleat 58 and cut, thereby releasing the magazine embodiment of FIGS. 7 and 8 from the two instruments and completing the loading of the needle and length of suture on the instruments.

The embodiment of FIG. 9 is similar to that of FIGS. 7 and 8 and like component parts have the same reference numbers followed by a prime ('). The only difference in the FIG. 9 embodiment of the magazine is that its longitudinal length is extended. The larger length of the base makes it easier to handle. Also, the needle 82 is held on the base in an opposite orientation to the base than that of the previous embodiment so that the needle may be grasped by the stitching instrument from outside the tubular interior of the base. This also requires that the suture extend outside the base from the needle 82. As shown in FIG. 9, the projections 96' hold the needle 82 at an intermediate portion of the needle with the needle opposite tips 86, 88 projecting laterally outward from the pair of projections. The length of suture 84 extends from the needle along the exterior surface of the base 92' and is wrapped in a pattern of loops adjacent the base proximal end 94'. From the pattern of loops the free end of the suture is wrapped around the spool 100'.

In use, the needle 82 is first gripped between the arms 20, 22 of the stitching instrument without inserting the instruments through the interior bore of the base 92'. With the needle gripped between the stitching instrument arms, the distal ends of the two instruments are then inserted through the base interior bore from the base proximal end 94'. The pattern of wrapped suture loops is then slipped off the base proximal end 94' and onto the distal end 46 of the knot-tying instrument inner tubular member. The base is then removed from the distal ends of the instruments and moved along the length of the two instruments toward the cleat 58 on the knot-tying instrument and the free end of the suture is wrapped around the cleat. The suture is then cut free from the two instruments, thereby completing the loading of the needle and length of suture on the instruments.

While the present invention has been described by reference to specific embodiments, it should be understood that modifications and variations of the invention may be constructed without departing from the scope of the invention defined in the following claims.

What is claimed:

1. An apparatus for loading a needle onto a stitching instrument and for holding a loop of suture attached to the needle, the apparatus comprising:

a needle and a length of suture secured thereto;

a base having a longitudinal length with opposite proximal and distal ends and a passageway extending through the base between the proximal and distal ends, the passageway being configured to enable insertion of a stitching instrument through the passageway from the base proximal end toward the base distal end, the base having an exterior surface holding a loop formed in the length of suture adjacent the proximal end of the base where insertion of a stitching instrument through the passageway will also insert the stitching instrument through the loop of suture; and the base having a holder spaced longitudinally from the loop of suture and positioned adjacent the distal end of the base, the holder being configured for holding the needle on the base where the needle can be removed from the holder by a stitching instrument inserted through the passageway.

2. The apparatus of claim 1, wherein:

the base has a tubular configuration and the passageway is a bore extending through the base.

3. The apparatus of claim 1, wherein:

a spool is mounted on the base for holding a length of the suture wrapped on the spool.

4. The apparatus of claim 1, wherein:

the exterior surface of the base is configured to enable sliding the loop of suture over the exterior surface and off one of the proximal and distal ends of the base.

5. An apparatus for loading a needle onto a stitching instrument and for loading a length of suture onto a suture tying instrument, the apparatus comprising:

a needle having a length of suture attached thereto;

a base having a longitudinal length;

first and second projections on the base positioned toward one end of the base longitudinal length, the first and second projections having a spacing therebetween that is sufficiently small to enable insertion of the needle in the spacing between the first and second projections to hold the needle in a position on the base where the needle can be removed from the projections by a stitching instrument;

opposing sidewalls on the base positioned toward an opposite end of the base spaced longitudinally from the first and second projections, the suture is wrapped in at least one loop around the opposing sidewalls and the opposing sidewalls have a spacing therebetween that is sufficiently large to enable insertion of a suture tying instrument between the opposing sidewalls and through the loop of suture wrapped around the opposing sidewalls.

6. The apparatus of claim 5, wherein:

the opposing sidewalls on the base are opposite sides of a tube, the tube having a longitudinal center axis and the loop of suture is wrapped around the tube.

7. The apparatus of claim 5, wherein:

the longitudinal spacing of the first and second projections from the opposing sidewalls is sufficient to enable insertion of a stitching instrument and a suture tying instrument together through the opposing sidewalls and the loop of suture wrapped around the opposing sidewalls to load the loop of suture on the suture tying instrument and to grasp the needle held by the first and second projections with the stitching instrument.

8. An apparatus for loading a needle onto a stitching instrument and for loading a length of suture onto a suture tying instrument, the apparatus comprising:

a needle having a length of suture attached thereto;

a base;

means on the base for holding the needle in a position on the base where the needle can be removed from the means for holding the needle by a stitching instrument;

means on the base for holding the length of suture attached to the needle in a position on the base where the length of suture can be removed from the means for holding the suture and loaded onto a suture tying instrument;

the base has a longitudinal length, the means for holding the suture is positioned toward one end of the base longitudinal length and the means for holding the needle is positioned toward an opposite end of the base longitudinal length;

the means for holding the suture includes opposing sidewalls on the base, the suture is wrapped at least one loop around the opposing sidewalls and the opposing sidewalls have a spacing therebetween that is sufficiently large to insert a suture tying instrument between the opposing sidewalls and through the loop of suture wrapped around the opposing sidewalls;

the means for holding the needle includes first and second projections on the base spaced longitudinally from the opposing sidewalls, the first and second projections have a spacing therebetween that is sufficiently small to enable insertion and wedging of the needle in the spacing between the first and second projections to hold the needle.

9. The apparatus of claim 8, wherein:

the opposing sidewalls on the base are opposite sides of a tube, the tube having a longitudinal center axis and the loop of suture is wrapped around the tube.

10. The apparatus of claim 8, wherein:

the longitudinal spacing of the first and second projections from the opposing sidewalls is sufficient to enable insertion of the stitching instrument and the suture tying instrument together through the opposing sidewalls and the loop of suture wrapped around the opposing sidewalls to load the suture on the suture tying instrument and to grasp the needle held by the first and second projections with the stitching instrument.

11. A method of loading a needle onto a stitching instrument and for loading a length of suture attached to the needle onto a suture tying instrument, the method comprising the steps of:

loading the stitching instrument and the suture tying instrument from a magazine, the magazine having first and second projections with a spacing therebetween and a pair of opposing sidewalls also having a spacing therebetween, the needle is positioned on the magazine wedged in the spacing between the first and second projections and the suture is positioned on the magazine wrapped in at least one loop around the opposing sidewalls;

loading the stitching instrument by grasping the needle with the stitching instrument and pulling the needle from the spacing between the first and second projections with the stitching instrument; and, loading the suture tying instrument by inserting the suture tying instrument between the opposing sidewalls and the loop of suture wrapped around the opposing sidewalls, and then sliding the at least one loop of suture off the opposing sidewalls and onto the suture tying instrument.

12. The method of claim 11, further comprising the step of:

inserting the stitching instrument and the suture tying instrument together between the opposing sidewalls and the loop of suture wrapped around the opposing sidewalls, and then grasping the needle with the stitching instrument and sliding the loop of suture off the opposing sidewalls and onto the suture tying instrument.

13. The method of claim 11, further comprising the steps of:

inserting the stitching instrument and the suture tying instrument together between the opposing sidewalls and the loop of suture wrapped around the opposing sidewalls, then sliding the loop of suture off the opposing sidewalls and onto the suture tying instrument, then removing the suture tying instrument and the stitching instrument together from between the opposing sidewalls, and then grasping the needle with the stitching instrument and pulling the needle from the spacing between the first and second projections with the stitching instrument.

14. The method of claim 11, further comprising the step of:

inserting the stitching instrument through a center bore of the suture tying instrument, and then inserting the stitching instrument and the suture tying instrument together between the opposing sidewalls and the loop of suture wrapped around the opposing sidewalls.

15. The method of claim 14, further comprising the step of:

inserting the stitching instrument and the suture tying instrument together between the opposing sidewalls and the loop of suture wrapped around the opposing sidewalls, the loop of suture forming a part of a knot in the suture.

\* \* \* \* \*